United States Patent [19]

Holmes

[11] Patent Number: 5,242,974
[45] Date of Patent: Sep. 7, 1993

[54] POLYMER REVERSAL ON SOLID SURFACES

[75] Inventor: Christopher P. Holmes, Sunnyvale, Calif.

[73] Assignee: Affymax Technologies N.V., Curacao, Netherlands

[21] Appl. No.: 796,727

[22] Filed: Nov. 22, 1991

[51] Int. Cl.$^5$ .................. C08F 283/00; C08G 63/48; C08G 63/91
[52] U.S. Cl. ................. 525/54.11; 530/333; 530/334; 530/335; 530/336; 530/337
[58] Field of Search ............ 525/54.11; 530/333, 530/334, 335, 336, 337

[56] References Cited

U.S. PATENT DOCUMENTS

| | | | |
|---|---|---|---|
| 4,722,906 | 2/1988 | Guire | 436/501 |
| 5,004,781 | 4/1991 | Rink | 525/54.11 |
| 5,064,907 | 11/1991 | Bronstert et al. | 525/54.11 |
| 5,066,716 | 11/1991 | Robey et al. | 525/54.11 |
| 5,143,854 | 9/1992 | Pirrung et al. | 436/518 |

FOREIGN PATENT DOCUMENTS

WO90/15070 12/1990 PCT Int'l Appl.
WO92/10092 6/1992 PCT Int'l Appl.

OTHER PUBLICATIONS

Fodor et al., *Science* (1991) 251:767-773.
Geysen et al., *J. Imm. Meth.* (1987) 102:259-274.
Bodanszky, *Principles of Peptide Synthesis*, springer-Verlag, 1984, pp. 208-229.
Rovero et al., *Tetrahedron Letters* (1991) 32:2639-2642.
McMurray, *Tetrahedron Letters* (1991) 32:7679-7682.

*Primary Examiner*—Nathan M. Nutter
*Attorney, Agent, or Firm*—Kevin R. Kaster; Vernon A. Norviel; Lauren L. Stevens

[57] ABSTRACT

A method for cyclization and reversal of the polarity of polymers on a substrate. The method provides for the formation of a polymer on a substrate (2) with a tether molecule (4). Through unmasking of a protective group (PG$_2$) a cyclic polymer (6) is formed. Through cleavage of an appropriate bond, a polarity reversed polymer (8) is formed. The method finds particular application in the formation of, for example, peptides and oligonucleotides.

24 Claims, 6 Drawing Sheets

POLYMER REVERSAL ON SOLID SURFACES

BACKGROUND OF THE INVENTION

The interaction of a molecular recognition element (MRE) or receptor with a surface-bound ligand varies substantially depending on how the ligand is presented. One important consideration in the presentation of a ligand to a receptor is the polarity of the ligand. In other words, a polymer/ligand will interact with a receptor differently in many instances when one "end" of the polymer is presented than when the opposite end is presented by the substrate. Such differential interaction is well known in the art for antibodies and corresponding antigens as well as enzymes and corresponding enzyme substrates (see Walsh, *Enzymatic Reaction Mechanisms*, W. H. Freeman and Co., New York, 1979, incorporated herein by reference for all purposes, for various examples of this differential interaction for enzymes and enzyme substrates).

Many molecules of biological interest, such as peptides, oligonucleotides, and carbohydrates, have an inherent polarity. For example peptides have an inherent polarity at their N and C termini, while oligonucleotides have inherent polarity in their 3' and 5' termini. Oligosaccharides also have an inherent polarity, having at least one hydroxyl group at one "end" and an anomeric center, with substantially different chemical reactivity at the other. The choice of which "end" of the polymer is to be tethered to a substrate during synthesis is generally governed by the chemistry required to build the polymer using solid-phase synthesis techniques. Peptides, for example, are frequently anchored to a substrate via their carboxyl terminus and the chemical synthesis proceeds on the terminal amino group (termed C to N or "Merrifield" synthesis) whereas nucleotides frequently have their 3' end anchored and the synthesis proceeds on the 5' end. Oligosaccharide solid-phase synthesis likewise proceeds with one end anchored and the other end available for reaction during synthesis.

Use of surface-bound ligands as a screening tool has necessitated the development of novel chemistries to provide for the presentation of polymers with both complementary polarities. For instance, proteins are typically sequenced from the amino terminus, but newer methods, see U.S. Pat. No. 5,064,767, incorporated herein by reference, provide for sequencing from the carboxy terminus. Some have proposed that the polymers be fully synthesized and then attached to a solid support with reversed polarity. This is often a labor-intensive and inefficient process. In the case of peptides, one may alternatively simply reverse the direction of synthesis of the polymer so as to anchor the molecule via the terminal amino group and proceed with the synthesis on the carboxyl terminus (termed "N to C synthesis"). There are several reasons why conventional polymer synthesis techniques cannot be easily adapted to the synthesis of polymers having their "opposite" terminus exposed, where exposed refers to the end of the polymer not attached to the solid support. In the case of peptides, for example, one problem, although not fully understood, is believed to be racemization of the growing peptide chain in a reversed polymer synthesis scheme. Racemization has been proposed to occur via intramolecular attack of the amide oxygen of the adjacent residue on the activated ester of the terminal residue, leading to an intermediate oxazolinone prone to racemization. While prevention of racemization may be possible, it may be a difficult, costly, or complex problem to solve. This problem may be particularly difficult to solve in the case of synthesis of polymers of substantial length. For example, in a 10-step synthesis there will often be 9 possible racemization events producing up to $2^9 = 512$ diastereomers.

In the case of nucleotide synthesis other problems are also not fully understood, but are believed to present difficulties. For example, there may be difficulty in selectively protecting the two types of hydroxyl groups (secondary versus primary) and the relative stabilities of the resultant compounds.

From the above it is seen that improved means and methods of synthesizing and presenting polymers on surfaces are desired.

SUMMARY OF THE INVENTION

Improved means and methods for synthesizing and presenting polymers on solid surfaces are disclosed. The methods are particularly useful in synthesizing polymers in reverse from a direction of normal synthesis, and for forming cyclic polymers. The invention also provides for a novel class of linkers having three sites of reactivity and orthogonal cleavage protocols.

According to one specific embodiment, the invention provides a method having a first step in which polymers are formed using standard polymer synthesis (Merrifield peptide synthesis or conventional nucleotide synthesis for example), or more advanced techniques, such as light-directed, spatially-addressable techniques. The polymers thus formed have a first polarity. Thereafter, the method provides for the unmasking of a reactive moiety on a tether molecule linking the polymer(s) to the surface. This activation allows for subsequent cyclization of an exposed end or region of the polymer to the reactive moiety on the linker. The method may optionally involve cleavage of the bond anchoring the polymer to the tether (the "Y-T" bond shown below), whereby a reversed sequence is formed, i.e., whereby the polarity of the molecule is reversed from the first polarity.

Accordingly, one embodiment of the invention provides for a method of synthesizing a polymer on a substrate comprising the steps of, on a surface of the substrate, providing a molecule having the general formula:

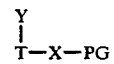

where X and Y are first and second reactive sites, respectively, T is a tether molecule, and PG is a first protective group; coupling a polymer to the reactive site Y; removing the protective group PG; and coupling a portion of the polymer to the tether at the first reactive site. The method may further provide for the step of reversing the polarity of the polymer by separating the polymer from the reactive site Y. In some embodiments of the invention, a protecting group on X is unnecessary because X is unreactive under the conditions used for coupling of monomers to X.

A further understanding of the nature and advantages of the inventions herein may be realized by reference to the remaining portions of the specification and the attached drawings.

DETAILED DESCRIPTION OF THE INVENTION

TABLE OF CONTENTS

Figure 1A:
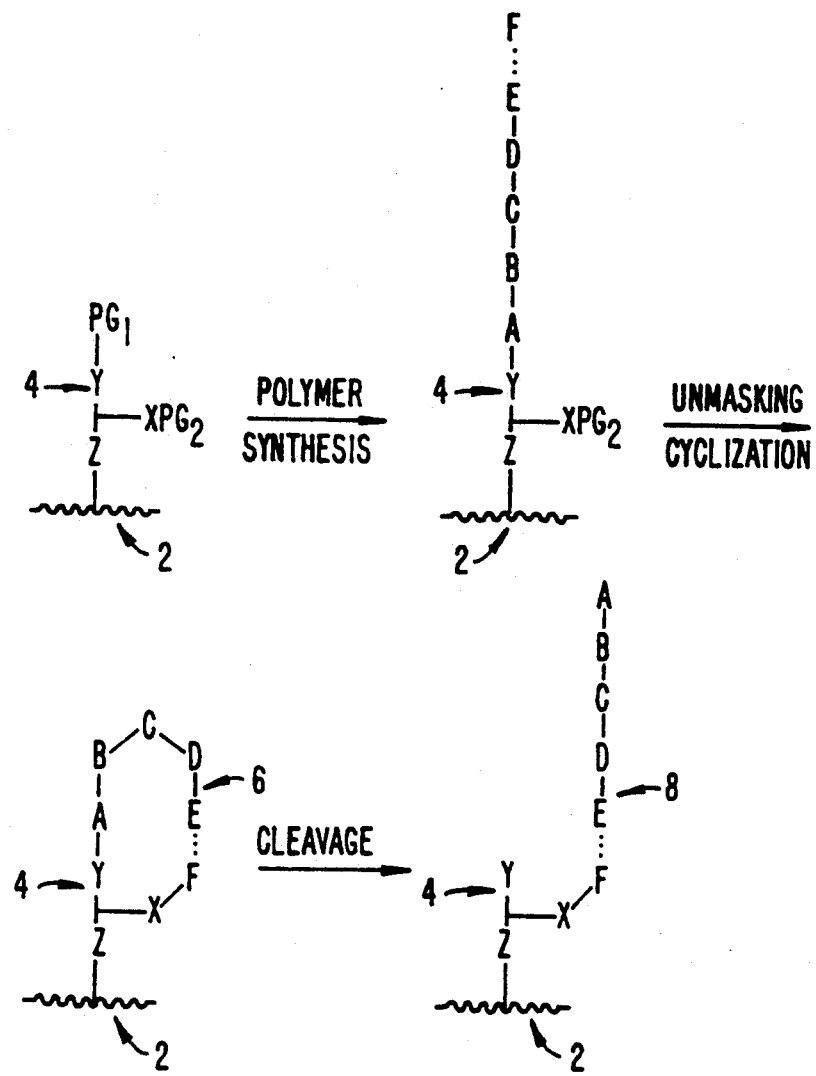
FIGS. 1a and 1b are overall flow diagrams illustrating one aspect of, the invention.

I. Definitions and Terminology
II. Overall Description of the Invention
III. Detailed Description
   of Preferred Embodiments
   A. Protective groups
      1. Conventional Peptide Synthesis
      2. VLSIPS ™ Peptide Synthesis
      3. Conventional Oligonucleotide
         Synthesis
      4. VLSIPS ™ Oligonucleotide Synthesis
      5. Other Polymers
   B. Cyclization
   C. Tether Molecules
      1. Peptides
      2. Oligonucleotides
      3. Specific Tether Molecules
IV. Use of the Synthesized Polymers
V. Examples
   A. Tether Attachment-
      Overall Description
   B. First Specific Embodiment
   C. Second Specific Embodiment
VI. Conclusion

I. Definitions and Terminology

The following terms are intended to have the following general meanings as they are used herein:

1. Ligand: A ligand is a molecule that is recognized by a particular receptor. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, cofactors, drugs, lectins, sugars, oligonucleotide, nucleic acids, oligosaccharides, proteins, and monoclonal antibodies.

2. Monomer: A member of the set of small molecules which can be joined together to form a polymer, especially those having an inherent polarity. The set of monomers includes but is not restricted to, for example, the set of common L-amino acids, the set of D-amino acids, the set of synthetic or natural amino acids, the set of nucleotides and the set of pentoses and hexoses. As used herein, monomers refers to any member of a basis set for synthesis of a polymer. For example, dimers of the 20 naturally occurring L-amino acids form a basis set of 400 monomers for synthesis of polypeptides. Different basis sets of monomers may be used at successive steps in the synthesis of a polymer. The invention is described herein primarily with regard to the preparation of molecules containing sequences of monomers such as amino acids or nucleic acids, but could readily be applied in the preparation of other polymers. Such polymers include, for example, polysaccharides, phospholipids, and peptides having either $\alpha$-, $\beta$-, or $\omega$-amino acids, heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure. Polysaccharides, for example, refer herein to a carbohydrate which can be hydrolyzed into many monosaccharides. Polynucleotides refer to molecules containing a series of nucleotide monomers.

3. Peptide: A polymer in which the monomers are alpha amino acids and which are joined together through amide bonds, alternatively referred to as a polypeptide. In the context of this specification it should be appreciated that the amino acids may be, for example, the L-optical isomer or the D-optical isomer. Peptides are often two or more amino acid monomers long, and often 4 or more amino acids long, often 5 or more amino acids long, often 10 or more amino acids long, often 15 or more amino acids long, and often 20 or more amino acid monomers long, for example. Standard abbreviations for amino acids are used (e.g., P for proline). These abbreviations are included in Stryer, *Biochemistry, Third Ed.*, 1988, which is incorporated herein by reference for all purposes.

4. Receptor: A molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, enzymes, hormones, opiates, polysaccharides, cells, cellular membranes, and organelles. Receptors are sometimes referred to in the art as anti-ligands. As the term receptors is used herein, no difference in meaning is intended. A "ligand receptor pair" is formed when two macromolecules have combined through molecular recognition to form a complex.

5. Substrate or Support: A material or group of materials having a rigid or semi-rigid surface or surfaces. In many embodiments, at least one surface of the substrate will be substantially flat, although in some embodiments it may be desirable to physically separate synthesis regions for different polymers with, for example, wells, raised regions, pins, etched trenches, or the like. According to other embodiments, the substrate(s) will take the form of beads, resins, gels, microspheres, or other geometric configurations. The substrate is alternatively referred to herein as a support.

6. Protective Group: A material which is bound to a molecule and which may be selectively removed therefrom for exposure of a reactive group. A protective group generally prevents undesired reactions from taking place (such as coupling) until such time as the protective group is removed.

7. Predefined Region: A predefined region is a localized area on a substrate which is, was, or is intended to be used for formation of a selected polymer and is otherwise referred to herein in the alternative as a "selected"

region. The predefined region may have any convenient shape, e.g., circular, rectangular, elliptical, wedge-shaped, etc. For the sake of brevity herein, "predefined regions" are sometimes referred to simply as "regions." In some embodiments, a predefined region and, therefore, the area upon which each distinct polymer sequence is synthesized is smaller than about 1 cm$^2$ or less than 1 mm$^2$. In preferred embodiments the regions have an area less than about 10,000 $\mu$m$^2$ or, more preferably, less than 100 $\mu$m$^2$. Within these regions, the polymer synthesized therein is preferably synthesized in a substantially pure form. In additional embodiments, a predefined region can be achieved by physically separating the regions (i.e., beads, resins, gels, etc.).

8. Substantially Pure: A polymer is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor. Preferably the region is sufficiently pure such that the predominant species in the predefined region is the desired sequence. According to preferred aspects of the invention, the polymer is 5% pure, more preferably more than 10% pure, preferably more than 20% pure, more preferably more than 80% pure, more preferably more than 90% pure, more preferably more than 95% pure, where purity for this purpose refers to the ratio of the number of ligand molecules formed in a predefined region having a desired sequence to the total number of molecules formed in the predefined region.

9. Polarity: Refers herein to the characteristic of a polymer which has at least a first and a second end, each end having distinctive characteristics. For example, peptides are said to have polarity due to the distinctive characteristics of their N and C termini. Oligonucleotides by way of further example have inherent polarity due to the distinctive characteristics of their 3' and 5' termini. Saccharides have an inherent polarity due to the distinctive chemical reactivity characteristics of the hydroxyl and anomeric termini of saccharides. Most monomers of a polymer show polarity, such as in, e.g., amino acids, nucleotides and saccharides. As used herein, "polarity" and "orientation" are to be considered synonymous.

10. Tether: A molecule which is coupled to a substrate and a polymer, directly or indirectly, and which has at least one reactive site thereon that may be selectively activated for coupling of an exposed portion of the polymer to the reactive site. Such tethers provide additional functionality in preferred embodiments such as for the functionalization of a solid support in order to allow for the polymer synthesis, and for de-coupling of a polymer after cyclization for polarity reversal.

11. Activator: Refers herein to an energy source or reagent which selectively renders one or more reactive sites active, or cleaves a selected bond. One example of an activator is a reagent such as a mild base which removes materials such as fluorenylmethyloxycarbonyl (FMOC) or a strong acid which removes certain protective groups such as BOC derivatives, side chain protective groups, and polymer linkage groups. Another illustration of an activator is light. Other examples of activators include ion beams, electric fields, magnetic fields, electron beams, x-ray, and biological activators such as enzymes, and the like.

12. Linker: Refers to a molecule or group of molecules attached to a substrate and spacing a synthesized tether and/or polymer from the substrate.

13. Reactive Group: Refers to a portion of a molecule which, under selected circumstances performs a desired coupling or cleavage reaction with another moiety. Such coupling may be via covalent, or other types of bonds.

14. Abbreviations: The following abbreviations are intended to have the following meanings:
BOC = benzyloxycarbonyl
BOP = benzotriazol-1-yloxytris(dimethylamino) phosphonium hexafluorophosphate
DCC = dicyclohexylcarbodiimide
DDZ = dimethoxydimethylbenzyloxy
DMT = dimethoxytrityl
FMOC = fluorenylmethyloxycarbonyl
HBTU = 2-(1H-benzotriazol-1-yl)-1,1,3,3-tetramethyluronium hexafluorophosphate
NV = nitroveratryl
NVOC = 6-nitroveratryloxycarbonyl and other photoremovable groups
PG = protective group
TFA = trifluoroacetic acid II. Overall Description of the Invention According to the invention herein, reversal of the polarity of a polymer and/or cyclization of the polymer is achieved through the use of appropriate protective group manipulation. According to a specific embodiment, the polarity of a polymer synthesis is reversed, i.e., a previously exposed terminus of the polymer is attached directly or indirectly to the substrate, while a previously directly attached terminus or portion of the polymer is placed in an exposed position.

According to one aspect of the invention the polymer molecules are synthesized with a first polarity on a substrate, and a reactive group on a tether in the polymer molecules is selectively activated. Thereafter, a region, usually a terminal end of the polymer, cyclizes to the tether at the activated site. Optionally, an initial bond joining the polymer to the surface is cleaved, whereby the initially bound group is placed in an exposed position such that the polarity of the polymer is reversed. Specific embodiments of the invention utilize photocleavable or photoactivatable groups as protective groups, while other embodiments use additionally or in combination with the photoactivatable or photocleavable groups a protective or cleavable group that is activated upon exposure to selected reagents such as an acid, base, or biological reagents such as enzymes.

One embodiment of the invention provides for a tether with one, two, three, or more sites of reactivity. A first site (Z) is used to anchor the tether molecule, directly or indirectly via linker molecules to a substrate. A second site (Y) is used to synthesize the polymer with a first polarity. A third site (X) is used to cyclize the polymer by bonding a portion of the polymer to the third site.

According to some embodiments of the invention, the tether has at least one protective group for protection of the third site (X), although a greater number of protective groups will be used according to some embodiments of the invention. For example, one protective group is used in some embodiments for side chain protection on the polymer. Another protective group is used in some embodiments for protection of the end of the polymer on which synthesis is taking place. Still another protective group is used in forming the original linkage between the polymer and tether, while still additional protective groups will be used to form the linkage between the support or any linker molecules and the tether molecule.

It will be recognized that not all protective groups will be used in all embodiments, and that in some embodiments one or more of the protective groups will be the same group. For example, in some embodiments the same protective group is used in formation of the bond between the substrate and tether as is used in the synthesis of the polymer. By way of further example, if the goal is to stop at the cyclized polymer stage, the group between the tether and the polymer becomes unnecessary. By way of still further example, side chain deprotection may be combined with the final cleavage of the linker.

Figure 1B:
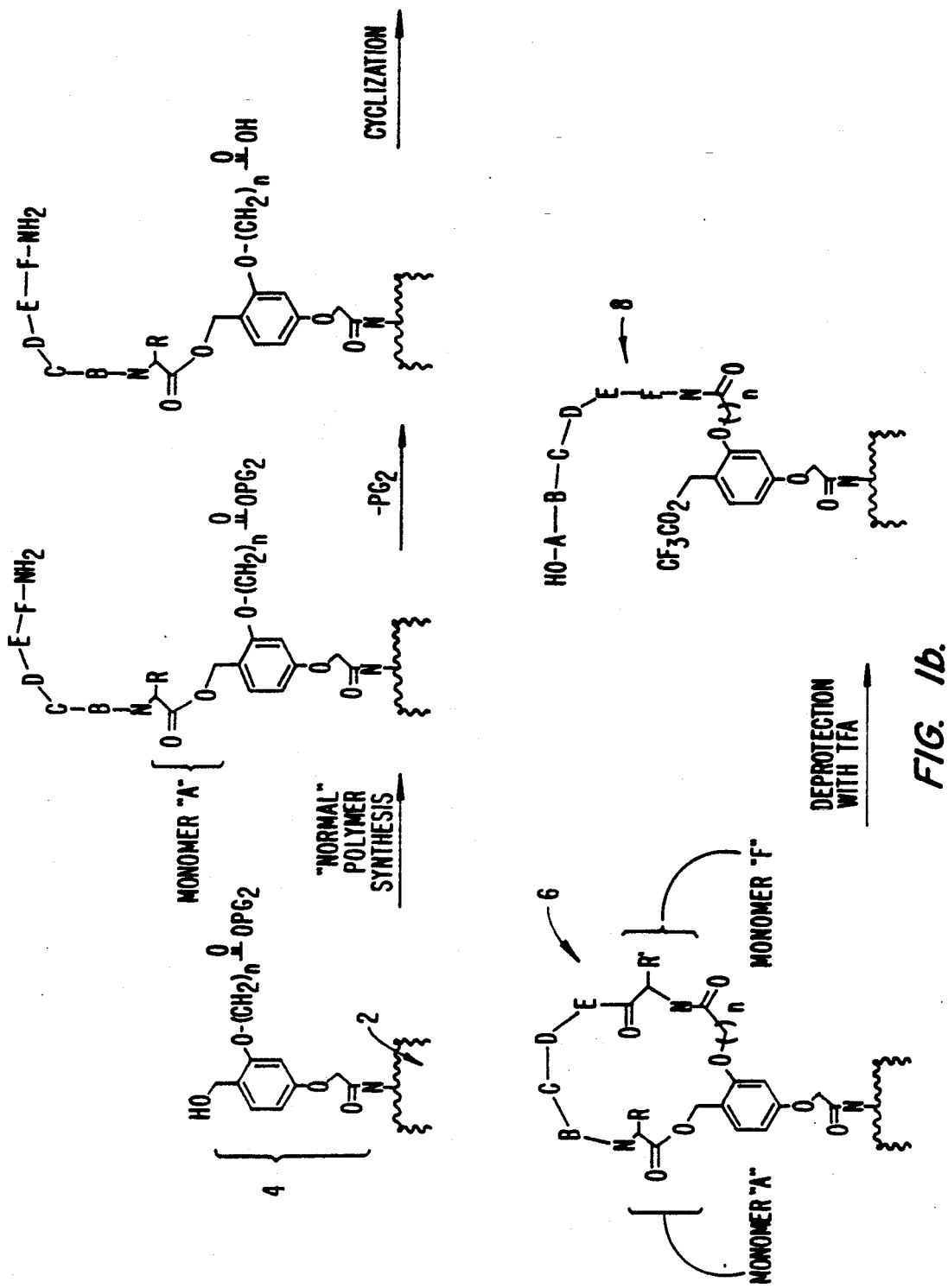

FIG. 1a provides an overall illustration of one embodiment of the invention, while FIG. 1b provides an overall illustration of the invention as applied to peptide synthesis. In FIG. 1 and elsewhere in this specification, "PG" refers to a protective group, X, Y, and Z refer to the various reactive sites discussed above, and A, B, C, D, E, and F refer to various monomers or groups of monomers.

As shown in FIGS. 1a and 1b, the process is conducted on a substrate 2. A tether molecule 4 is coupled to a surface of the substrate. The tether molecule includes one or more reactive sites such as a reactive site Z which is used to couple the tether to the substrate. The tether is also provided with a reactive site X having a protective group $PG_2$ thereon. The tether molecule further includes a reactive site Y, optionally with a protective group $PG_2$ thereon.

In a first step, a polymer synthesis is carried out on the reactive site Y. According to some embodiments, conventional polymer synthesis techniques are utilized such as those described in Merrifield, "Solid Phase Peptide Synthesis," *J. Am. Chem. Soc.*, (1963) 85:2149-2154, incorporated herein by reference for all purposes. A wide variety of techniques may be used in alternative embodiments. For example, according to one embodiment, a variety of polymers with different monomer sequences are synthesized on the substrate. Such techniques may involve the sequential addition of monomers or groups of monomers on the growing polymer chain, each monomer of which may also have a reactive site protected by a protective group.

A variety of such methods are available for synthesizing different polymers on a surface. For example, Geysen et al., "Strategies for Epitope Analysis Using Peptide Synthesis," *J. Imm. Meth.*, (1987) 102:259-274, incorporated herein by reference for all purposes, describes one commonly used technique for synthesizing different peptides using a "pin" technique. Other techniques include those of Houghten et al., *Nature* (1991) 354:84-86, incorporated herein by reference. In some embodiments, advanced techniques for synthesizing polymer arrays are utilized such as those described in copending application Ser. No. 07/796,243 filed on the same day as the present application, or light-directed, spatially-addressable techniques disclosed in Pirrung et al., PCT application No. WO 90/15070; U.S. application Ser. No. 07/624,120; and Fodor et al., "Light-Directed Spatially-Addressable Parallel Chemical Synthesis," *Science* (1991) 251:767-773, all incorporated herein by reference for all purposes, such techniques being referred to herein for purposes of brevity as the VLSIPS ™ (Very Large Scale Immobilized Polymer Synthesis) synthesis technique.

During polymer synthesis one may not want the activator used to remove $PG_1$ (if any) on the Y reactive site, and on reactive sites of the growing polymer chain, if any, to remove the X protective group $PG_2$. Merely by way of example, the activator used to remove $PG_2$ may be a first chemical reagent, while the activator used to remove the protective group $PG_1$, may be a second, different chemical reagent. By way of further example, the activator used to remove one of the protective groups may be light, while the activator used to remove the other protective group may be a chemical reagent, or both activators may be light, but of different wavelengths. Of course, other combinations will be readily apparent to those of skill in the art on review of this disclosure.

In some embodiments, the bond between the reactive site Y and the first monomer is cleavable upon exposure to an activator such as a selected reagent, irradiation with light, or the like. In the specific case of peptide synthesis, for example, one form of standard Merrifield peptide synthesis employs a fluorenylmethyloxycarbonyl (FMOC) on the growing end of the peptide. "Standard" techniques generally involve cycles of mild base treatment to remove the FMOC for growth of the polymer chain. According to this specific embodiment, the protective group on the reactive site X is removed not by a weak base, but by another activator such as light, fluoride ion, weak acid, strong base, a biological reagent, an ion beam, or the like. The reactive site Y is optionally cleavable from the monomer A upon exposure to still another activator such as light of a different wavelength or a strong acid.

As shown in FIGS. 1a and 1b, by virtue of proper protective group selection and exposure to only the $PG_1$ activator, the reactive site X is protected during polymer synthesis and does not take part in the initial portion of the process. Also, the reactive site Y remains bound to the monomer A.

Optionally, side chain protective groups are provided on the monomers to prevent branching during synthesis. The side chain protective groups are selected to remain in position during the synthesis of the polymer chain, and may be removed upon exposure to the same or a different activator as the activator used to cleave the Y-A bond. In a preferred embodiment, the side chain protective groups are removed only upon exposure to the same activator as the one used for cleavage of the Y-A bond, such as acid. Accordingly, during the synthesis step side chain protection is also maintained.

As shown in the second portion of FIGS. 1a and 1b, the synthesis step of the process, which will frequently include many substeps of deprotection/ coupling, results in a polymer of a desired length, schematically illustrated by the polymer "ABCDE . . . F" in FIGS. 1a and 1b. It is to be understood that a polymer with 5 or more monomers is illustrated in FIG. 1, but fewer monomers will be utilized according to some embodiments.

In a preferred embodiment, the last monomer on the polymer will be a "flexible" monomer to aid or enhance the cyclization process. Preferred flexible monomers are relatively long, as compared to other monomers of the same class, and undergo highly efficient cyclization chemistry. This flexible monomer becomes the new linker between the peptide and tether after cyclization.

In a next step of the process, the protective group $PG_2$ on the X reactive site is removed. In addition, the reactive site on the last monomer F is rendered active, if necessary. As shown in FIGS. 1a and 1b, the reactive site on the selected monomer will then react with the reactive site X, forming a cyclic polymer 6. In a preferred embodiment for peptide synthesis, the protective group $PG_1$ is removed with light.

In a next, optional, step of the process, the substrate is treated for cleavage of the Y-A bond and, in preferred embodiments, for simultaneous removal of any side chain protective groups. Merely by way of example in one embodiment of peptide synthesis, a strong acid (up to 100% TFA) is used both the removal of the side chain protective groups and cleavage of the Y-A bond.

This step of the process results in a polymer bound to the substrate, but with reversed polarity from the polarity as the polymer was originally synthesized. Thus, through the use of a conventional linkage to the support and an orthogonal group as the protective group of the second site of reactivity on the tether, reversed polarity peptides are obtained. Alternatively, any orthogonal chemically- or biologically-cleavable group would work as an appropriate protective group for X.

III. Detailed Description of Preferred Embodiments
A. Protective porous

It will be recognized that choice of the various protective groups will be dictated by the type of polymer which is to be synthesized and the desired synthesis technique. Therefore, for example, oligonucleotides will often have different protective groups than will peptides, oligosaccharides, and the like. In addition, conventional solid-phase syntheses techniques without the use of photoprotective groups will utilize different protective groups than VLSIPS TM light-directed synthesis techniques. Still further, if the desired polymer is the cyclized polymer, the protective groups may be selected differently than if the final product is to be of reversed polarity. Specific examples of protective groups are discussed in detail below. Table 1 summarizes the various protective groups used according to most preferred embodiments of the invention, along with cleavable bond descriptions for polymer reversal.

TABLE 1
Preferred Protective Group Selections

| Synthesis | $PG_1$/Activator | $PG_2$/Activator | Cleavable Bond Activator |
|---|---|---|---|
| Standard Peptide | FMOC/Base | NVOC or other photochem./base or light | Acid |
| Standard Peptide | BOC/Acid | NVOC or other photochem./base or light | Acid |
| Standard Nucleotide | DMT/Mild Acid | NVOC or other photochem./light | Base |
| VLSIPS TM Peptide | NVOC (or other photochemical protecting groups)/Light | FMOC or other base sens./base | Acid |
| VLSIPS TM Nucleotide | NV or NVOC/Light | DMT or other acid sens./acid | Base |

1. Conventional Peptide Synthesis

One technique of standard Merrifield peptide synthesis employs fluorenylmethyloxycarbonyl (FMOC) on the growing end (amino terminus) of the polymer and one or more of a variety of side chain protective groups. According to preferred embodiments herein, such techniques generally utilize mild base treatment to remove the FMOC ($PG_1$) for peptide growth, and strong acid (up to 100% TFA) for both removal of the side chain protective groups and cleavage of the tether/polymer bond. According to some embodiments, cleavage of the tether utilizes mild acid, without removal of side chain protective groups, which are removed with a stronger acid. Base or light is used to remove the protective group $PG_2$, which may be, for example, NVOC.

As shown herein, the method permits not only cyclization of the peptide, but also the use of conventional C terminal to N terminal synthesis techniques, while exposing the carboxyl end of the peptide after polymer reversal. In preferred embodiments, the peptide synthesis uses otherwise known peptide chemistry in which monomers are coupled to the exposed amino group during synthesis.

2. VLSIPS TM Peptide Synthesis

One embodiment of the invention utilizes a group $PG_1$ which is removable with a first wavelength of light and a second photocleavable group $PG_2$ which requires a different wavelength for deprotection of X. Preferably such groups utilize wavelengths >300 nm in order to avoid conflicting with protective groups in use during polymer synthesis and to avoid damage to sensitive amino acids. Photocleavable groups at different wavelengths are used for X-Y bond breaking. Alternatively, some embodiments employ a base- or fluoride-sensitive protective group. Other such materials include FMOC, $\beta$ cyanoethyl, t-butyldiphenylsilyl, and a plethora of others apparent to those of skill in the art. Again, an A-Y linkage resistant to acid cleavage allows access to the cyclized nucleotides.

Exemplary $PG_1$ and $PG_2$ groups for various peptide synthesis techniques are listed in Table 2, along with their activators.

TABLE 2
Peptide Synthesis
Protective Groups/Activators

| $PG_1$/Activator | $PG_2$/Activator |
|---|---|
| BOC/Acid | NVOC/Light |
| BOC/Acid | FMOC/Base |
| FMOC/Base | NVOC/Light |
| NVOC/Light | BOC/Acid |
| NVOC/Light | FMOC/Base |
| NVOC/Light | DMT/Acid |
| FMOC/Base | BOC/Acid |

3. Conventional Oligonucleotide Synthesis

Standard nucleotide synthesis involves the use of dimethoxytrityl (DMT) on the growing end of the polymer and a variety of protective groups on the bases and the phosphates. Monomers are added to the 5' end of the growing oligonucleotide. Mild acid is used to cleave DMT whereas either base (ammonium hydroxide) or thiophenol is used to cleave the exocyclic amine protective groups on the bases and the phosphate protective groups. Concentrated ammonium hydroxide is commonly used to cleave the polymer from the substrate. Once again, a photocleavable group on the second site of reactivity of the tether is preferred. An A-Y linkage resistant to base cleavage allows access to the cyclized nucleotides.

4. VLSIPS TM Oligonucleotide Synthesis

Either two photocleavable groups $PG_1$ and $PG_2$ are utilized, or an additional orthogonal chemically- or biologically-cleavable group is utilized. A preferred embodiment uses DMT for removal of $PG_2$.

Exemplary $PG_1$ and $PG_2$ groups for various oligonucleotide synthesis techniques are listed in Table 3, along with their activators.

TABLE 3

| Oligonucleotide Synthesis Protective Groups/Activators | |
|---|---|
| $PG_1$/Activator | $PG_2$/Activator |
| DMT/Acid | NVOC/Light |
| NV or NVOC/Light | DMT/Acid |

It should be recognized that NVOC, as utilized in the tables above, may refer to a broad class of groups including dimethoxy benzyl, dimethoxydimethyl benzyl, α-methyl phenoxycinnamates, nitroveratryl, nitropiperonyl, and the like. Other groups are described in copending application Ser. No. 07/624,120, previously incorporated herein by reference. DMT refers to one member of a broad class of acid-sensitive protecting groups, and for purposes of the present invention, any mild acid-labile protecting group is equivalent to DMT.

5. Other Polymers

Other polymers such as oligosaccharides will use the same or different protective groups such as those described in Greene, "Protecting Groups in Organic Synthesis," including silyl (removed with fluoride ion), β-cyanoethyl (removed with base), and acetal groups (removed with acid), as well as those listed in Tables 2 and 3, above.

B. Cyclization

Cyclization of the synthesized polymer back onto the tether is an important step in the process described herein, and requires attention to a number of factors. The primary factors are accessibility of the terminus of the polymer to the tether region, the efficiency of the cyclization process, the selectivity of the cyclization towards the terminal monomer unit or other desired monomer unit, the type of activation required to achieve cyclization, and importantly, the stability of the new bond formed.

There are numerous options for the type of bond formed in the cyclization process which can be generalized into two classes: those which continue the backbone motif (e.g., amide bond formation for peptides and phosphates for nucleotides) and those which employ novel linkage techniques. Cyclization may utilize, e.g., disulfides, esters, ureas, carbamates, carbonates, amides, thioesters, alkylation or acylation.

One means of cyclization provides for the use of a sulfide to disulfide conversion whereby free thiols are liberated on both the desired monomer and the tether and subsequently allowed to cyclize. This approach would be applicable for cyclization of, for example, peptides and certain other polymers.

For the cyclization of peptides, cyclization using an amide or urea bond is also a useful ring closure reaction. Liberation of a carboxyl group on the tether, activation via standard procedures (DCC, BOP, HBTU, etc.) and cyclization with the free terminal amino group to form an amide bond provides a straightforward process. According to one embodiment, generation of an isocyanate or thioisocyanate on the tether and intramolecular ring closure via urea or thiourea bond formation is utilized. According to a preferred embodiment, capping of the terminal amino acid with a flexible, amine containing group such as 6-aminocaproic acid allows one to minimize difficulties associated with inflexible polymers.

Cyclization may also occur via phosphates or ester bond formation. These options are particularly useful for nucleotide applications. Any of the conventional coupling reactions (phosphoramidite, phosphotriester, phosphodiester, phosphite triester, etc.) evident to those skilled in the art may be employed in the cyclization reaction. According to a preferred aspect of the invention, as with the peptide polymers, capping with a flexible monomer may enhance the cyclization process and allows for the introduction of alternative cyclization techniques. In addition, by designing the terminal nucleotide sequence to complement the starting sequence, one may be able to enhance cyclization by taking advantage of any internal folding which effectively brings the terminal region in close proximity to the tether region.

The above techniques are illustrative of methods for cyclization reactions. Clearly other cyclization techniques apparent to those of skill in the art could be employed. These may include other photochemical, biological, chemical, or other procedures.

C. Tether Molecules

1. Peptides

The most prevalent method of anchoring a growing peptide to a solid support relies on an acid-cleavable benzylic bond as the critical bond undergoing cleavage. There are many common resins which differ as to their compatibility to the standard protection protocols (BOC versus FMOC) and as to whether an amide or free acid is desired on the C terminus. These are described in commercial supply catalogs such as those by Amino-Tech.

2. Oligonucleotides

Figure 2A:
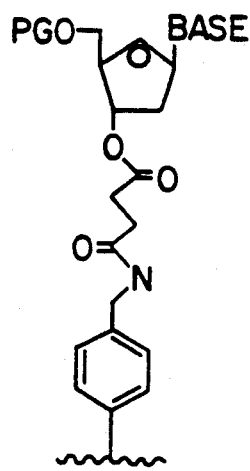
FIGS. 2a to 2c illustrate existing nucleotide tethers.
Figure 2B:
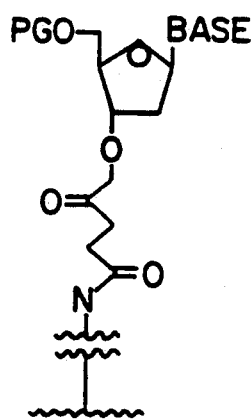
Figure 2C:
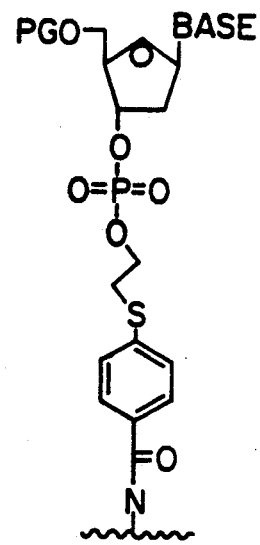
Figure 3A:
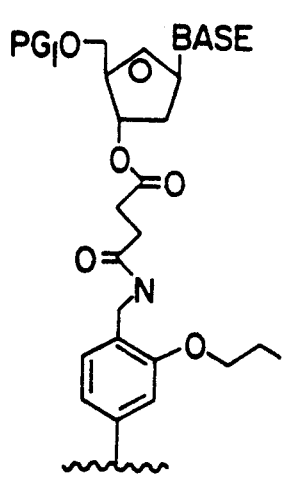
FIGS. 3a to 3c illustrate various novel nucleotide tethers.
Figure 3B:
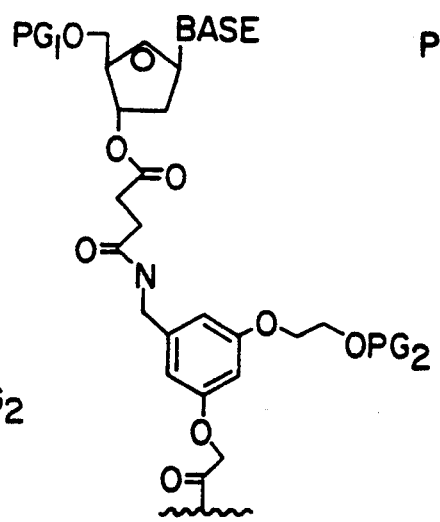
Figure 3C:
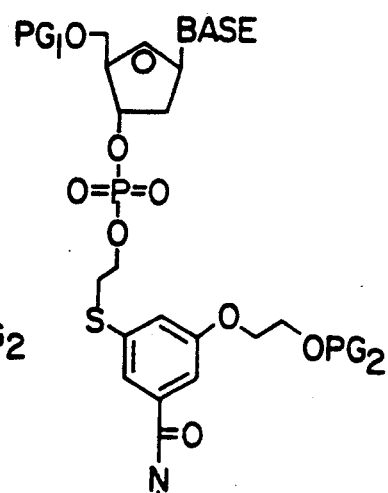

There are several common types of linkers, as depicted in FIGS. 2a to 2c such as polystyrene (FIG. 2a), controlled pore glass (FIG. 2b), and a CAMET linkage (FIG. 2c). Novel oligonucleotide linkers provided herein are illustrated in FIGS. 3a, 3b, and 3c.

3. Specific Tether Molecules

As discussed above, the tether molecules (T) will generally be of the formula:

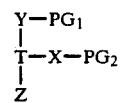

According to one specific embodiment, especially preferred for oligonucleotide synthesis, an aromatic tether (not limited to benzyl) is utilized of the general form:

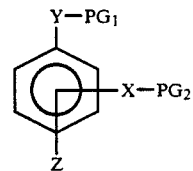

where:

X, Y are groups containing reactive sites individually selected from the group of O, NH, S, $CO_2$, S—$CH_2C$-$H_2O$, and $NHCOCH_2CH_2CO_2$; and Z is a group containing a reactive site selected from the group of halogen, O, NHS, S—CH₂CH₂O, and NHCOCH₂CH₂CO₂.

According to another embodiment, which is particularly preferred for peptide synthesis with acid cleavage for polarity reversal, the tether molecule is of the benzyl group of the form:

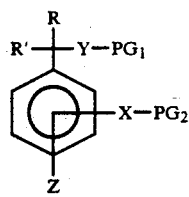

where:

R and R' are individually or both selected from the group consisting of H, methyl, alkyl (especially C₂ to C₈), aryl (including substituted phenyl, methoxy substituted phenyl), phenyl, bridged phenyl, and ring compounds, especially C₅ to C₁₅, which are formed by either 1) R or R' hooked together to form a ring, or 2) either R or R' linked to the phenyl group, thus forming a ring;

X, Y are groups containing reactive sites individually selected from the group of O, NH, S, CO₂, S—CH₂CH₂O, and NHCOCH₂CH₂CO₂; and Z is a group containing a reactive site selected from the group of halogen (i.e., in a halo alkyl), O, NHS, S—CH₂CH₂O, and NHCOCH₂CH₂CO₂

Some embodiments provide for the benzyl compound shown above with Y selected from the group consisting of O, NH, S, NHCOCH₂CO₂, and SCH₂CH₂O (the latter two being linkages especially preferred for nucleotides).

Preferred embodiments of the invention provide for a 1-2-4 tether structure:

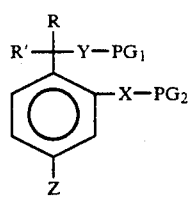

where R'60 and R are preferably as described above.

Alternatively, the tether may be:

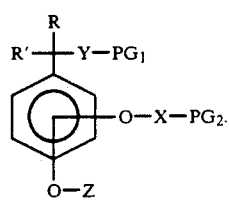

Alternatively the tether may be a 1-benzyl 4-alkoxy tether;

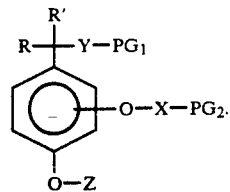

According to another preferred embodiment the tether is a 1-benzyl 2,4 dialkoxy tether:

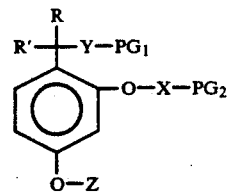

where R and R' are preferably as set forth above, and X and Z are preferably alkyl, especially C₂ to C₆ or aryl.

Most preferred groups PG₁ and PG₂ in the above compounds are:
PG₁: BOC, FMOC, NVOC, DMT, NV, FM
PG₂: BOC, FMOC, NVOC, DMT, NV, FM
A most preferred tether is:

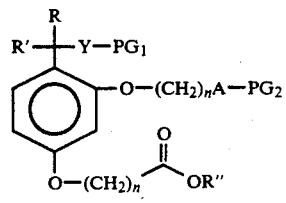

where R and R' are selected from the above-described groups; n is preferably 0 to 10; A is preferably O, N, S, CO, or CO₂; and R" is selected from the group of H, NHS, substituted aryl.

A most preferred linker is:

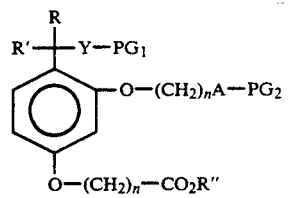

where:
the substrate binds to the acid at the para position;
R and R' are selected from the group of H, alkyl (especially C₂ to C₈), aryl, bridged ring;
A is O, N, B, CO, or CO₂;
n=1 to 10 and preferably about 4; and
PG₁ is BOC and PG₂ is FMOC or
PG₁ is NVOC and PG₂ is FMOC or
PG₁ is FMOC and PG₂ is NVOC or
PG₁ is DMT and PG₂ is NVOC or
PG₁ is NVOC and PG₂ is DMT or
PG₁ is BOC and PG₂ is NVOC.

The above compounds are also useful in the reversal of nucleotide polymers, except that the linkage between the aryl group and the reactive group Y need not be a benzylic linkage, because one can link Y directly to the aryl ring. For dialkoxy methyl groups about less than 10% and preferably about 1-2% TFA is used for cleavage, preferably for less than 5 hours and more preferably about 1-2 hours.

Most preferred embodiments of the invention utilize tethers of the form:

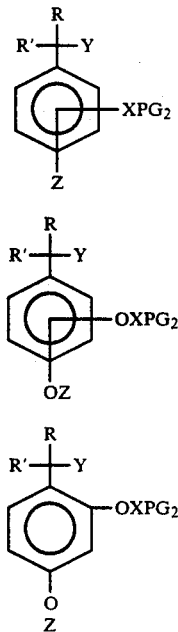

where:
Y=OH, OPG$_1$, NH$_2$, NHPG$_1$, SH, SPG$_1$, CO$_2$H, or CO$_2$PG$_1$;
R, R'=H, methyl, phenyl, substituted phenyl, bridged phenyl; and
X=(CH$_2$)$_n$APG$_2$, n=0 to 10, and A=O, N, S, CO$_2$.
Preferably:
OH, OPG$_1$, NH$_2$, or NHPG$_1$;
R, R'=H, methyl, phenyl;
X=(CH$_2$)$_n$APG$_2$, n=0 to 10, A=O, N, S, CO$_2$; and
PG$_2$=NVOC, NV, FMOC, FM, BOC, B, DMT
PG$_1$=NVOC, PG$_2$=FM, and A=CO$_2$
PG$_1$=FMOC, PG$_2$=NV, and A=CO$_2$
PG$_1$=BOC, PG$_2$=NV, and A=CO$_2$
PG$_1$=NVOC, PG$_2$=DMT, and A=0
PG$_1$=DMT, PG$_2$=NV, and A=0.

IV. Use of the Synthesized Polymers

The polymers synthesized according to the invention herein will have a variety of uses. Among the uses of the cyclic and polarity reversed polymers will be screening of the polymers for binding with a receptor, nucleotide sequencing, and the like. Screening of peptides, for example, to determine their affinity with a receptor is discussed in detail in PCT application No. WO 90/15070, previously incorporated by reference herein. Sequencing may also use the method disclosed in U.S. Pat. No. 5,064,767, previously incorporated herein by reference.

V. Examples

A. Tether Attachment—Overall Description

Figure 4:
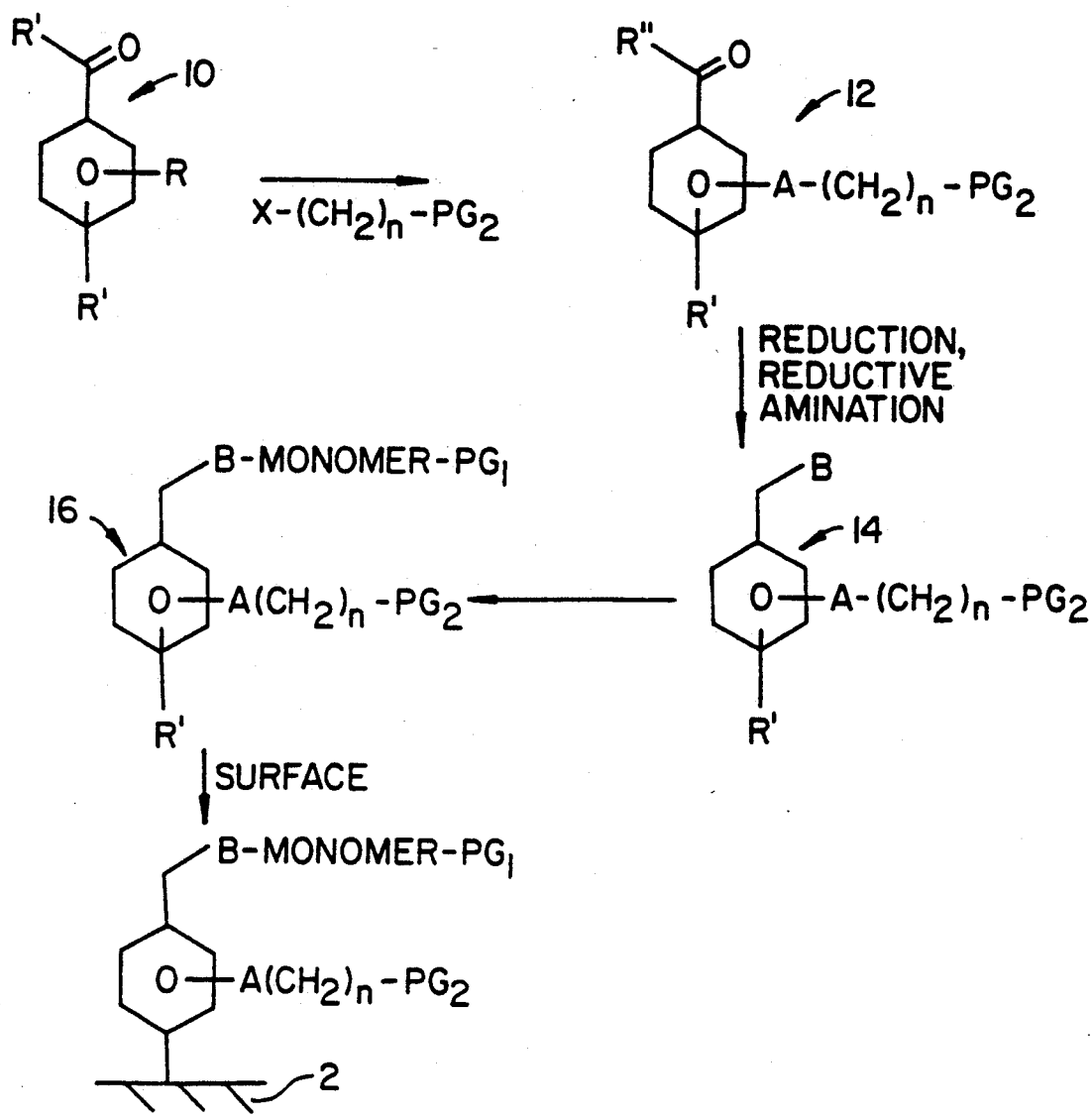
FIG. 4 provides an exemplary process for tether attachment and use.

FIG. 4 illustrates a process for attachment of a tether to a substrate. Material 10 is utilized as a starting material, where R and R' are individually selected from the group of OH, NH$_3$, SH, halogen, CO$_2$R''; and R'' is selected from the group of H, alkyl (esp. C$_2$ to C$_8$) and aryl. Such para OH compounds are described in, for example, Wymann et al., 1988 *Symp. Commun.* (1988) 18:1379-1381. The material 10 is reacted in a solution of X—(CH$_2$)—PG$_2$, where X is selected from the group of halo, OH, NH$_2$, SH, or the like to yield the compound 12, where A is OH N, S, or the like, depending upon the reactant used.

In the next step, the material 12 is reduced to yield the product 14 where B is selected from the group of OH, NH$_2$, SH, or halo, depending upon the reduction reaction utilized. It will be recognized by those of skill in the art that the first and second steps outlined in FIG. 4 can readily be reversed without departing from the scope of the invention herein.

The material 14 is then reacted in a solution containing a reactant having the formula:

to form the compound 16. The compound 16 is then exposed to a surface of a substrate 2 for binding thereto.

B. First Specific Embodiment

Figure 5:
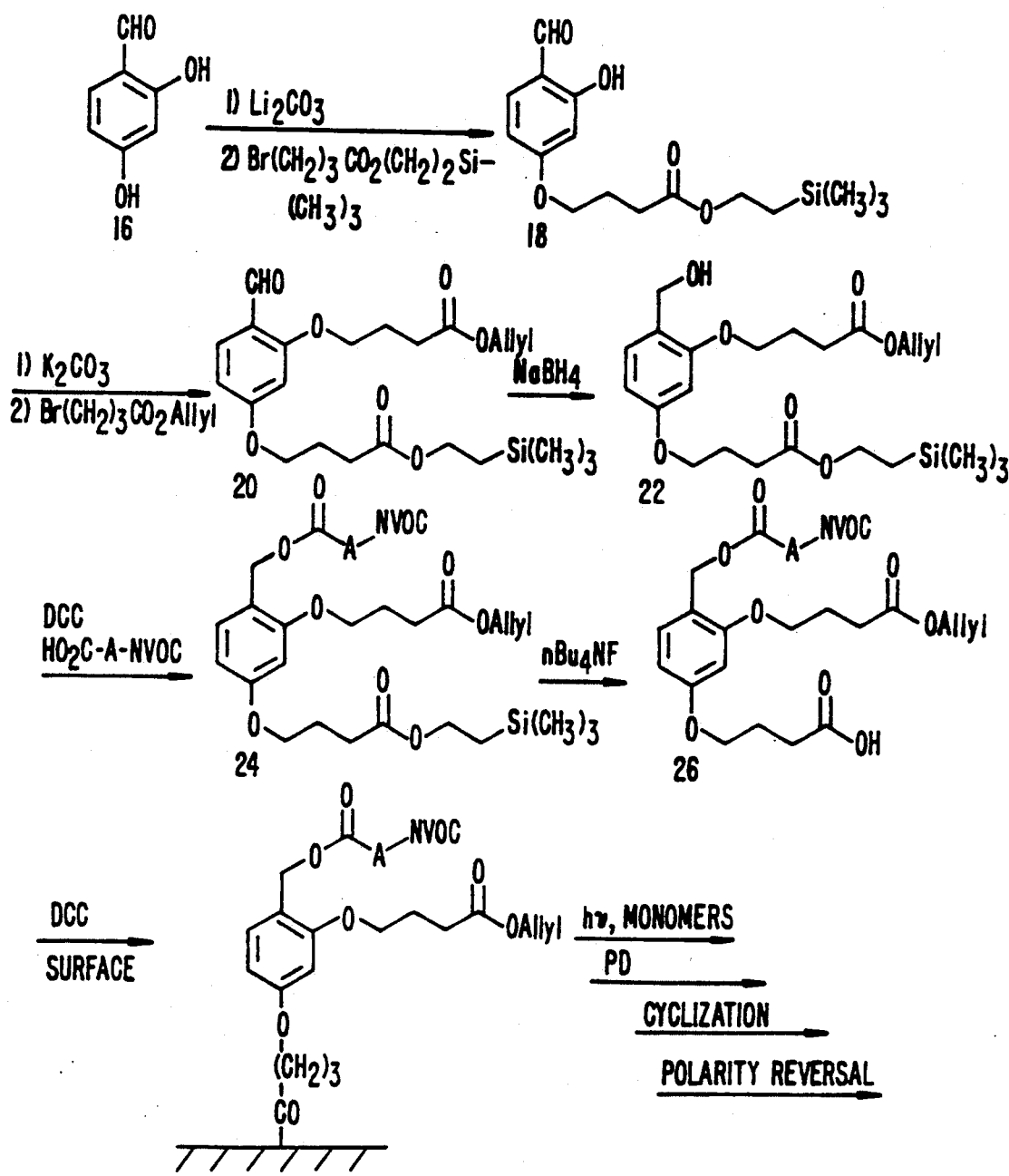
FIG. 5 illustrates a preferred process for tether attachment and use.

FIG. 5 illustrates a specific process which is proposed for use in accordance with the invention. In the description below Bz is intended to refer to a benzyl group, while FM is intended to refer to a fluorenylmethyl group.

In a first step, about 10 mmoles of compound 16 are reacted in a solution with 25 mmoles of Li$_2$CO$_3$ and 10 mmoles of ethyl 4-bromobutyrate in DMF at 80° C. for about 24 hours, resulting in the compound 18. Ten mmoles of the compound 18 are reacted with 25 mmoles of K$_2$CO$_3$ and 10 mmoles of 9-fluorenylmethyl 4-bromo-butyrate in DMF, also at about 80° C. for about 24 hours. This portion of the process results in a compound 20, of which 10 mmoles are reacted with 10 mmoles of Na$_2$BH$_4$ in ethanol at about room temperature for about 24 hours, resulting in the compound 22.

The compound 22, again about 10 mmoles, 20 is reacted with 10 mmoles of DCC and 10 mmoles of HO$_2$C-A-NVOC, where A is the first monomer terminating in OH, N, or S, in DMF at room temperature for about 24 hours, resulting in the compound 24. The compound 24 is refluxed with excess HCL (1 to 5 M, usually 2 to 3 M) in dioxane resulting in compound 26. The compound 26 is then reacted with a surface of the substrate in a DCC solution, to provide a surface-attached compound 28. The surface is then treated with light to couple additional monomers, in accordance with the procedures described in the copending applications incorporated by reference above. Cyclization is accomplished by exposing the completed substrate to base (about 20% piperidine in dichloromethane, followed by exposure to BOP), and polymer reversal is accomplished by exposing the substrate to a strong acid (about 1 to 100% TFA).

C. Second Specific Embodiment

Figure 6:
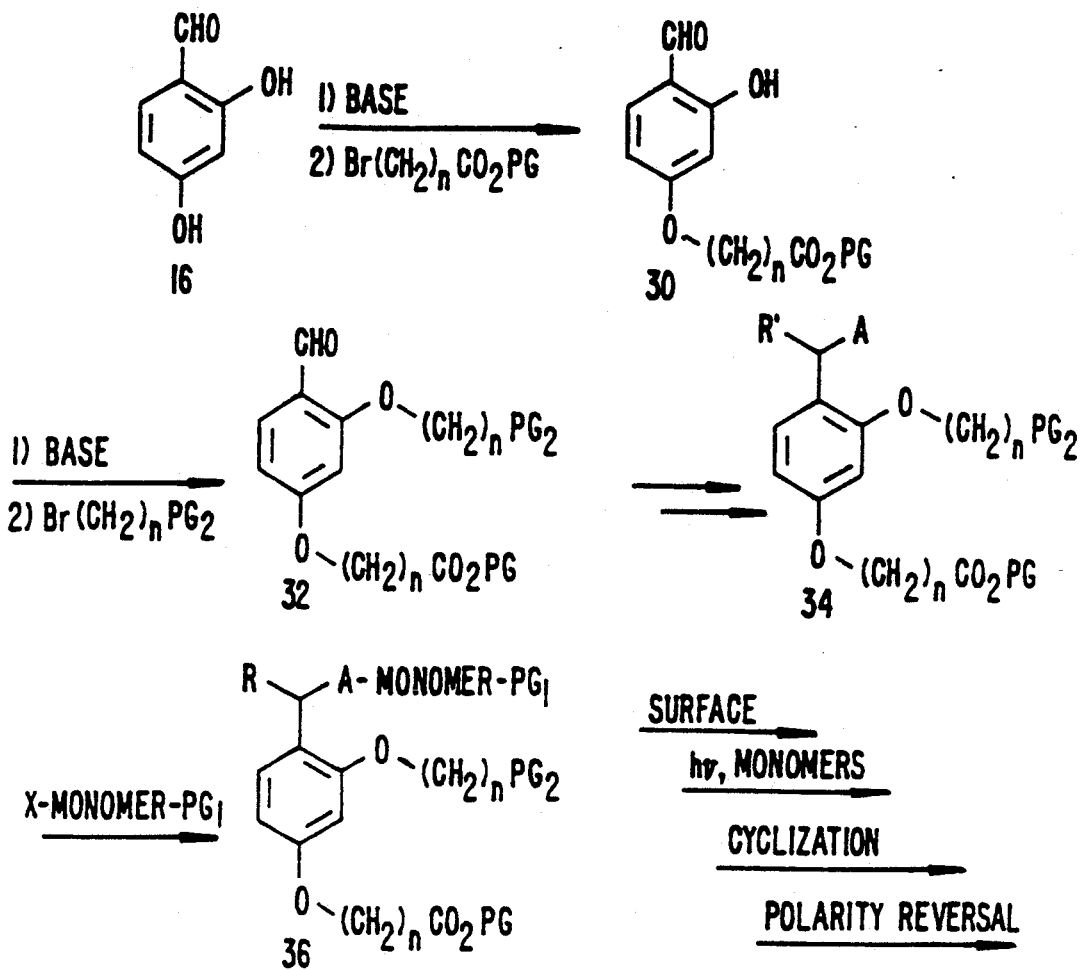
FIG. 6 illustrates a preferred process for tether attachment and use.
Figure 5:
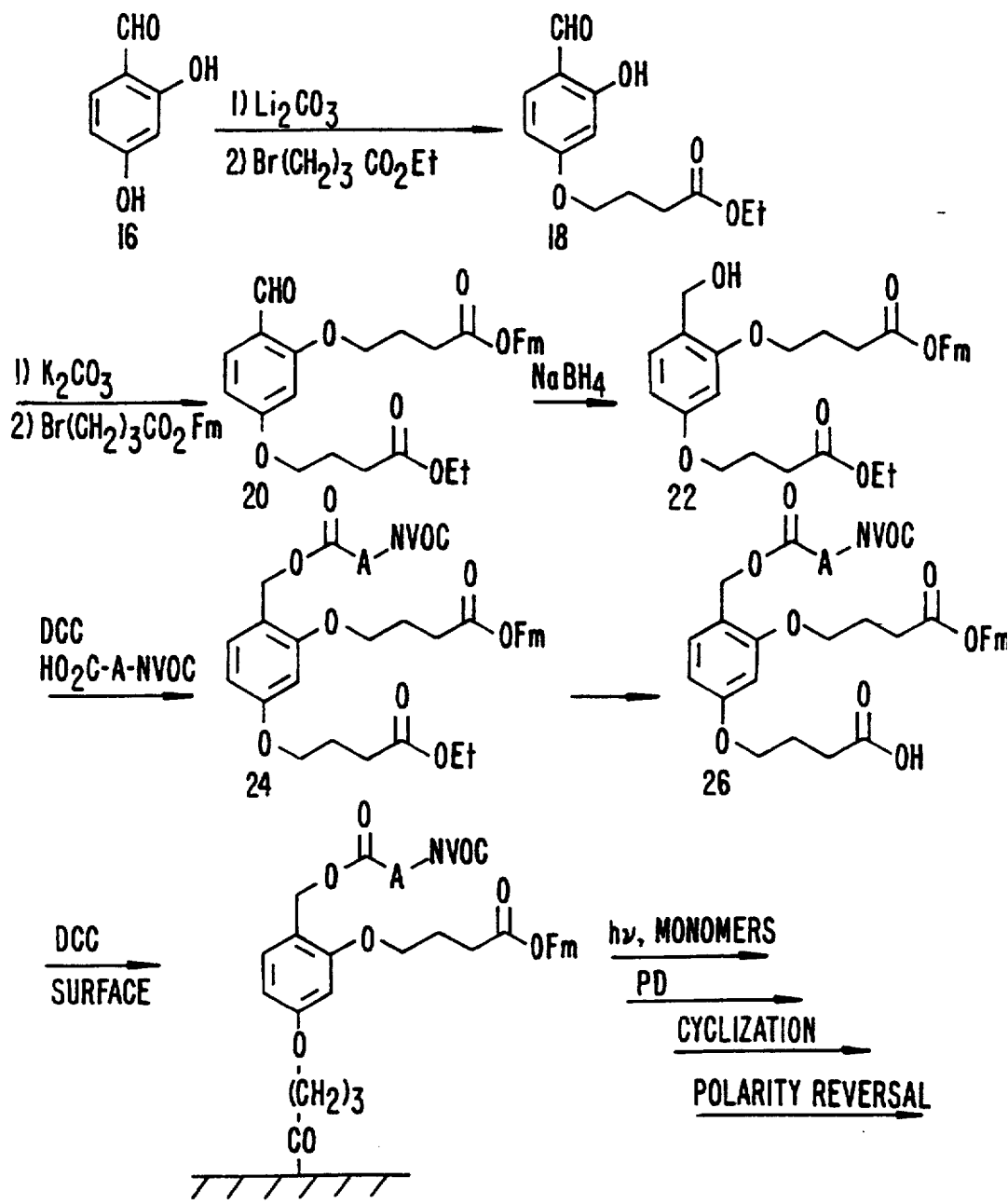

FIG. 6 illustrates another specific embodiment of the invention. In this case, the compound 16 is reacted in a basic solution of Br—(CH$_2$)$_n$—CO$_2$R (where n is about 2 to 8, and R is selected from the group of alkyl (C$_2$ to C$_8$), benzyl, and NHS), resulting in the compound 30. The compound 30 is reacted in a basic solution of Br—(CH$_2$)$_n$—PG$_2$ (n=2 to 8) to provide the compound 32.

The compound 32 is then reduced, resulting in the 34, where monomer unit A contains a reactive moiety selected from the group of OH, NH, SH, and halo; and R' is selected from the group of H, Me, alkyl ($C_2$ to $C_8$), substituted phenyl, and phenyl.

The compound 34 is then exposed to a monomer solution of X-monomer-$PG_1$, resulting in the compound 36. This compound is then subjected to additional monomer reactions, cyclization and, optionally, polymer reversal in accordance with the above description.

VI. Conclusion

It is seen that the above described methods and devices provide for improved and more versatile polymer synthesis on solid surfaces. It is to be understood that the above description is intended to be illustrative and not restrictive. Merely by way of example, the invention may be used in conjunction with the synthesis of a wide array of polymers, using a wide array of protective groups, and using a wide array of tether or link molecules. Also, there are numerous other applications that can readily be envisaged from the introduction of novel tethers into any solid-phase synthesis program. For example, one aspect of the invention would provide for a second orthogonal photocleavable bond as the anchor linking the first monomer to the support, allowing one to selectively cleave the assembled polymers off the surface. With the present invention, one can also simultaneously synthesize free N-terminus, cyclized, and free C-terminus peptides on a single solid support.

The scope of the invention should, therefore, be determined not with reference to the above description, but instead should be determined with reference to the appended claims along with their full scope of equivalents.

What is claimed is:

1. A method of synthesizing a polymer on a substrate comprising the steps of:
   a) on a surface of said substrate, having covalently attached thereto a molecule having the general formula:

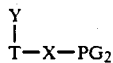

wherein said molecule is selected from the group consisting of:

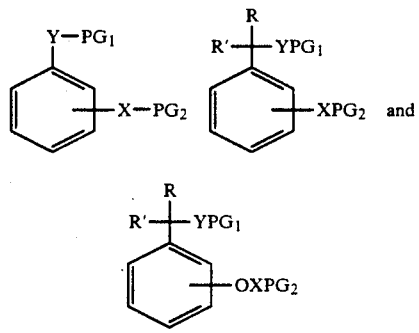

where:
   X and Y are first and second reactive sites, respectively, X is selected from the group consisting of —O—, —NH—, —S—, —$CO_2$—, —S—$CH_2$-$CH_2O$—, and —NHCO$CH_2$$CH_2$$CO_2$—; and Y is selected from the group consisting of —OH, —$NH_2$, —SH, —$CO_2H$, —S—$CH_2CH_2OH$, and NHCO$CH_2$$CH_2$$CO_2$H, wherein Y is protected with a protective group $PG_1$;

T is a tether molecule;
   $PG_1$ is a first protective group and is selected from the group consisting of BOC, FMOC, NVOC, DMT, NV, and FM;
   $PG_2$ is a second protective group and is selected from the group consisting of BOC, FMOC, NVOC, DMT, NV, and FM; and
   R and R' are independently selected from the group consisting of hydrogen, methyl, phenyl, and methoxyphenyl;

b) covalently coupling a polymer to said reactive site Y by:
   removing said first protective group $PG_1$ from said reactive site Y;
   covalently coupling a monomer to said reactive site Y, said first monomer having a monomer reactive site Y protected with a first protective group $PG_1$, wherein said first protective group $PG_1$ is selected from the group consisting of BOC, FMOC, NVOC, DMT, NV, and FM;
   repeating said steps of removing a protective group and coupling a monomer to form a polymer at said reactive site Y;

c) removing said second protective group $PG_2$; and
   d) covalently coupling a region of said polymer to said tether at said first reactive site to form a cyclic polymer.

2. A method as recited in claim 1 further comprising the step of cleaving said bond between T and Y whereby a polarity of said polymer is reversed.

3. The method as recited in claim 2 wherein said step of cleaving comprises the step of exposing said polymer to an acid.

4. The method as recited in claim 1 wherein said polymer is a peptide.

5. The method as recited in claim 4 wherein said polymer is a peptide and said monomer reactive site is an amino group.

6. The method as recited in claim 5 further comprising the step of cleaving said bond between T and Y whereby a polarity of said peptide is reversed.

7. The method as recited in claim 1 wherein said polymer is an oligonucleotide.

8. The method as recited in claim 1 wherein said polymer is an oligonucleotide and said monomer reactive site is a 5' end of said oligonucleotide.

9. The method as recited in claim 8 further comprising the step of cleaving said bond between T and Y whereby a polarity of said oligonucleotide is reversed.

10. The method as recited in claim 1 wherein said first protective group is NVOC and said second protective group is FMOC.

11. The method as recited in claim 1 wherein said first protective group is NVOC and said second protective group is BOC.

12. The method as recited in claim 1 wherein said first protective group is NVOC and said second protective group is DMT.

13. The method as recited in claim 1 wherein said first protective group is FMOC and said second protective group is NVOC.

14. The method as recited in claim 1 wherein said first protective group is DMT and said second protective group is NVOC.

15. The method as recited in claim 1 wherein said first protective group is NVOC and said second protective group is DMT, and said polymer is an oligonucleotide.

16. A method as recited in claim 1 wherein said molecule having the general formula:

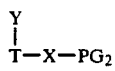

is a molecule having the general formula:

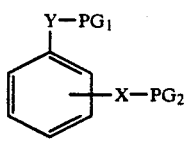

where:
X and Y are first and second reactive sites, respectively; and PG$_1$ and PG$_2$ are first and second protecting groups, respectively.

17. A method as recited in claim 1 wherein said molecule having the general formula:

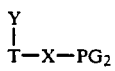

is a molecule having the general formula:

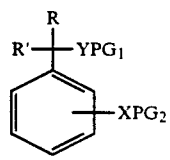

where:
X and Y are first and second reactive sites, respectively; PG$_1$ and PG$_2$ are first and second protecting groups, respectively; and R and R' are independently selected from the group consisting of hydrogen, methyl, phenyl, and methoxyphenyl.

18. A method as recited in claim 17 wherein said molecule having the general formula:

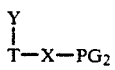

is a molecule having the general formula:

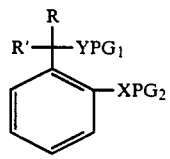

where:
X and Y are first and second reactive sites, respectively; PG$_1$ and PG$_2$ are first and second protecting groups, respectively; and R and R' are independently selected from the group consisting of hydrogen, methyl, phenyl, and methoxyphenyl.

19. A method as recited in claim 1 wherein said molecule having the general formula:

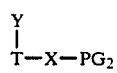

is a molecule having the general formula:

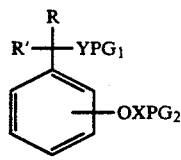

where:
X and Y are first and second reactive sites, respectively; PG$_1$ and PG$_2$ are first and second protecting groups, respectively; and R and R' are independently selected from the group consisting of hydrogen, methyl, phenyl, and methoxyphenyl.

20. A method as recited in claim 19 wherein said molecule having the general formula:

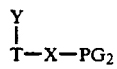

is a molecule having the general formula:

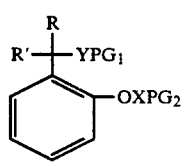

where:
X and Y are first and second reactive sites, respectively; PG$_1$ and PG$_2$ are first and second protecting groups, respectively; and R and R' are independently selected from the group consisting of hydrogen, methyl, phenyl, and methoxyphenyl.

21. A method as recited in of claim 1 wherein said first protective group is DMT or BOC and said second protective group is FMOC.

22. A method as recited in claim 1 wherein said first protective group is selected from the group consisting of DMT, BOC, and FMOC and said second protective group is selected from the group consisting of NVOC, dimethoxybenzyl, dimethoxydimethylbenzyl, α-methylphenoxycinnamates, nitroveratryl, and nitropiperonyl.

23. A method as recited in claim 1 wherein said first protective group is selected from the group consisting of NVOC, dimethoxybenzyl, dimethoxydimethylbenzyl, α-methylphenoxycinnamates, nitroveratryl, and nitropiperonyl and said second protective group is selected from the group consisting of DMT, BOC, and FMOC.

24. A method of synthesizing an oligopeptide on a substrate comprising the steps of:
a) on a surface of said substrate, having covalently attached thereto a molecule having the general formula:

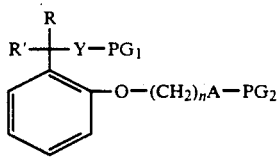

where:
R and R' are independently selected from the group or hydrogen, $C_2$-$C_8$ alkyl, phenyl, and methoxyphenyl;

Y is a reactive site selected from the group consisting of —OH, —NH$_2$, —SH, —CO$_2$H, —S—CH$_2$CH$_2$OH, and NHCOCH$_2$CH$_2$CO$_2$H and wherein Y is protected with a protective group PG$_1$ and;

A is oxygen, nitrogen, sulfur, CO, or CO$_2$;

n is 1 to 10;

PG$_1$ is a first protective group and is selected from the group consisting of BOC, FMOC, NVOC, DMT, NV, and FM; and PG$_2$ is a second protective group and is selected from the group consisting of BOC, FMOC, NVOC, DMT, NV, and FM;

b) repeating the steps of:
1) removing said protective group PG$_1$ to provide a first reactive site Y;
2) covalently coupling an amino acid to said first reactive site Y, said first amino acid having said reactive site Y protected with said protective group PG$_1$;

to form an oligopeptide at said first reactive site Y;

c) removing said protective group PG$_2$ to provide a second reactive site; and d) covalently coupling a region of said oligopeptide to said substrate bound molecule at said second reactive site to form a cyclic oligopeptide.

* * * * *

UNITED STATES PATENT AND TRADEMARK OFFICE
CERTIFICATE OF CORRECTION

PATENT NO. : 5,242,974

DATED : September 7, 1993

INVENTOR(S) : Christopher P. Holmes

It is certified that error appears in the above-indentified patent and that said Letters Patent is hereby corrected as shown below:

In the drawing

Delete drawing sheet Figure 5, and substitute therefor the consisting of Figure 5, as shown on the attached page.

Signed and Sealed this

Eighteenth Day of October, 1994

Attest:

BRUCE LEHMAN

Attesting Officer

Commissioner of Patents and Trademarks